United States Patent [19]
Alam

[11] Patent Number: 5,766,436
[45] Date of Patent: Jun. 16, 1998

[54] METHOD, A PROCESS, A DEVICE AND A KIT FOR LANE-BY-LANE FORMAT HORIZONTAL ELECTROPHORESIS

[76] Inventor: Aftab Alam, 9 Foxcliff Ct., St. Louis, Mo. 63011

[21] Appl. No.: 642,049

[22] Filed: May 6, 1996

[51] Int. Cl.⁶ ............................ G01N 27/26; G01N 27/447
[52] U.S. Cl. ............................ 204/456; 204/466; 204/470; 204/606; 204/616; 204/619; 204/620
[58] Field of Search ............................ 204/456, 466, 204/470, 606, 616, 609, 620

[56] References Cited

U.S. PATENT DOCUMENTS

| 3,497,441 | 2/1970 | Paksi | 204/470 X |
| 3,767,560 | 10/1973 | Elevitch | 204/616 |
| 5,569,369 | 10/1996 | Leffler et al. | 204/616 X |

*Primary Examiner*—Kathryn L. Gorgos
*Assistant Examiner*—John S. Starsiak, Jr.

[57] ABSTRACT

A method of electrophoresis and providing electrophoresis support medium in lane-by-lane formation, each lane having a sample loading well and for electrophoresis gel lanes are transferred to electrophoresis tank lane by lane and used for electrophoresis.

13 Claims, 6 Drawing Sheets

Fold up end

METHOD, A PROCESS, A DEVICE AND A KIT FOR LANE-BY-LANE FORMAT HORIZONTAL ELECTROPHORESIS

HISTORY OF THE INVENTION

Horizontal gel electrophoresis is widely used for analysis of proteins and nucleic acids. For horizontal gel electrophoresis slab type electrophoresis support mediums are prepared. Support medium contains a plurality of sample loading wells in which electrophoresis samples are loaded. One disadvantage of preparing slab type support medium is that if all of the sample wells are not utilized then at the end of electrophoresis the support medium will be discarded along with unutilized part of the slab support medium. Agarose is most widely used as electrophoresis support medium. Agarose is expensive and if a part of the slab support medium (agarose) is not used it is simply wasted. The way slab support mediums are prepared and used it is not possible to avoid wasting unutilized parts of slab support medium. In addition, after electrophoresis recovery of bands of molecules requires complicated use of knife to excise the biomolecule bands and extract biomolecules from the support medium. Therefore, there is a need for developing an electrophoresis method and support medium which eliminates waste of unutilized support medium and cut the cost of electrophoresis and in addition simplify recovery of bands of molecules.

This invention relates to a method of electrophoresis, a device, a process and a kit for preparing electrophoresis support medium which eliminates waste of electrophoresis support medium, improves and simplifies the recovery of molecules from the support medium. A yet another objective of the present invention is to provide a method and a device for regeneration of used electrophoresis support medium.

SUMMARY OF THE INVENTION

According to the present invention, there is provided a method of gel electrophoresis in which electrophoresis support medium is prepared and provided in lane-by-lane formation i.e. as individual gel lanes, each lane having at least one sample loading well. For electrophoresis one or more gel lanes are transferred to electrophoresis device and placed horizontally on the gel platform and used for electrophoresis. Sample loading well in the gel lanes are positioned to receive samples when gel lanes are horizontally positioned.

The invention further provides a device for assisting horizontal gel electrophoresis in lane by lane formation, the device comprising: a container having gel support medium, the support medium is provided as plurality of gel lanes each lane having at least one sample loading well to receive sample when gel lanes are positioned horizontally.

The invention further provides a gel support medium for assisting horizontal gel electrophoresis, the gel support medium comprising: a container having gel support medium provided as a plurality of gel lanes, each gel lane having at least one sample loading well.

The invention further provides a method of making a gel support medium in lane by lane formation and a device for cutting slab gel support medium into individual gel lanes. The device comprising: a tray for holding gel support medium, the tray having a means for positioning a gel comb for forming sample loading wells; and a gel slicing means for positioning over the tray to slice the slab gel support medium into individual lanes, the slicing means preferably having plurality of knifes either to run through the slab gel support medium or punched over the slab gel support medium.

DETAILED DESCRIPTION OF THE PREFERRED EMBODIMENT

Figure 2:
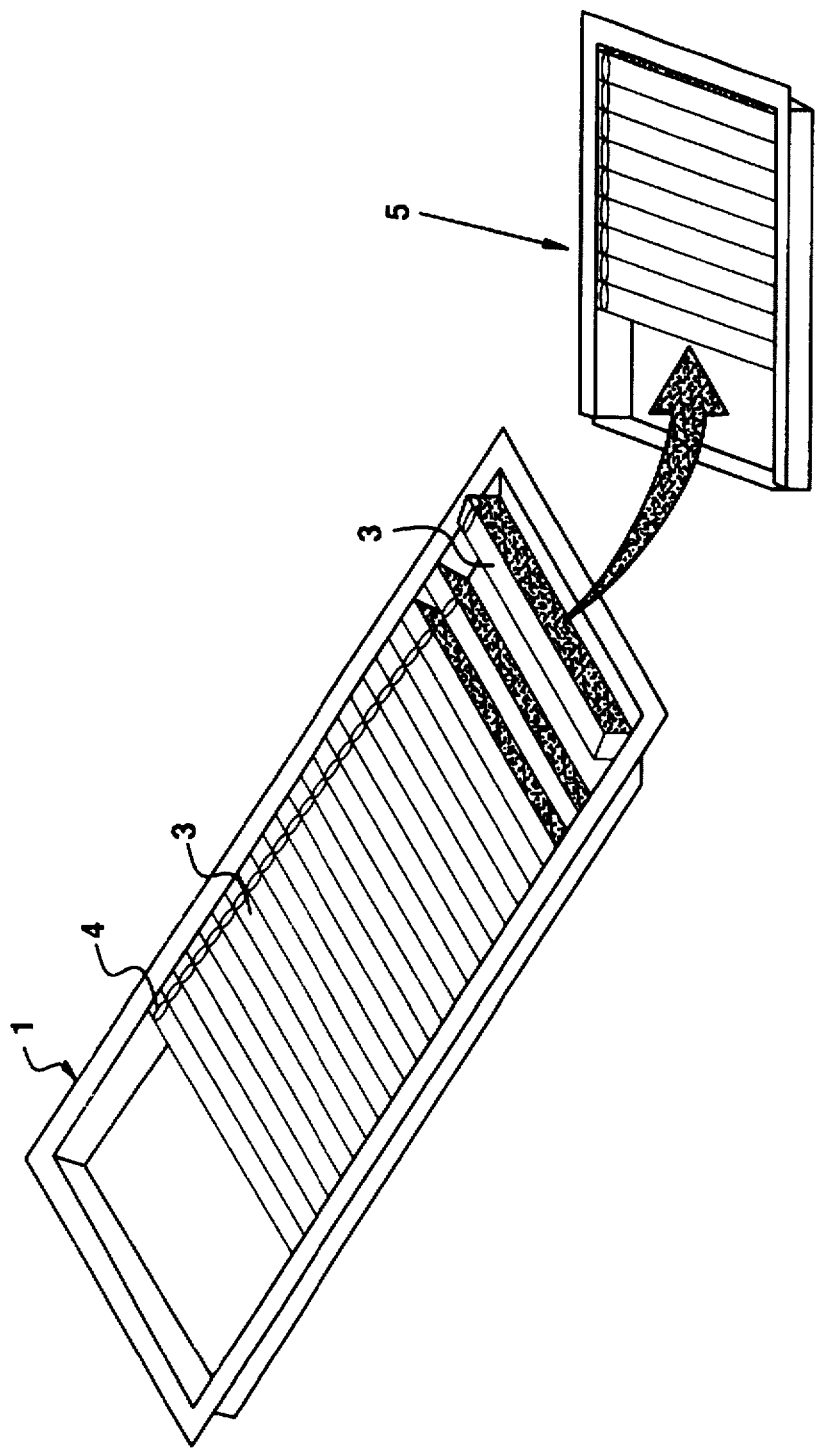
FIG. 2 shows gel lanes are transferred to a modified tray for electrophoresis.

According to the present invention, there is provided a method of electrophoresis in which electrophoresis support medium is prepared and provided as individual lanes, each lane contains at least one sample loading well. Support medium is generally agarose or other electrophoresis matrixes and polymerizing materials. The sample loading wells in gel lanes are positioned to receive samples when gel lanes are positioned horizontally on an electrophoresis device. One or more gel lanes are transferred to an electrophoresis device and placed horizontally on the gel platform and used for electrophoresis. When a plurality of gel lanes are used, the gel lanes are stacked together such that they appear as a contiguous support medium as shown in FIG. 2.

Figure 1:
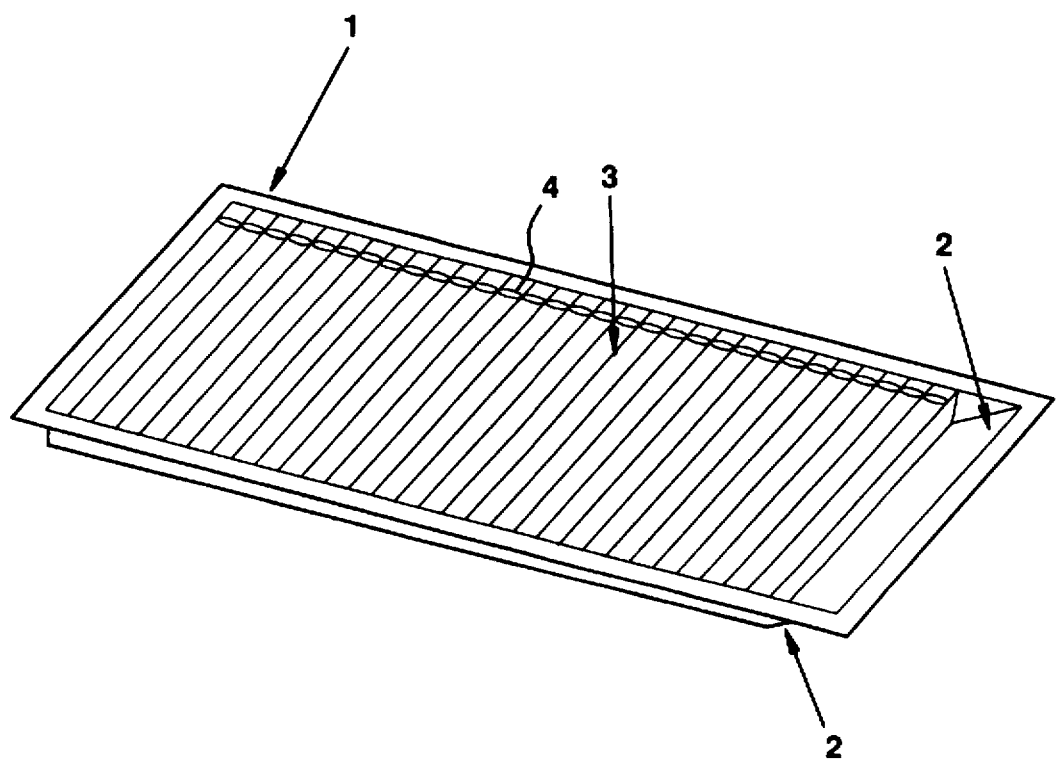
FIG. 1 shows a tray containing gel support medium prepared in lane-by-lane formation, i.e. as individual lanes.
Figure 3:
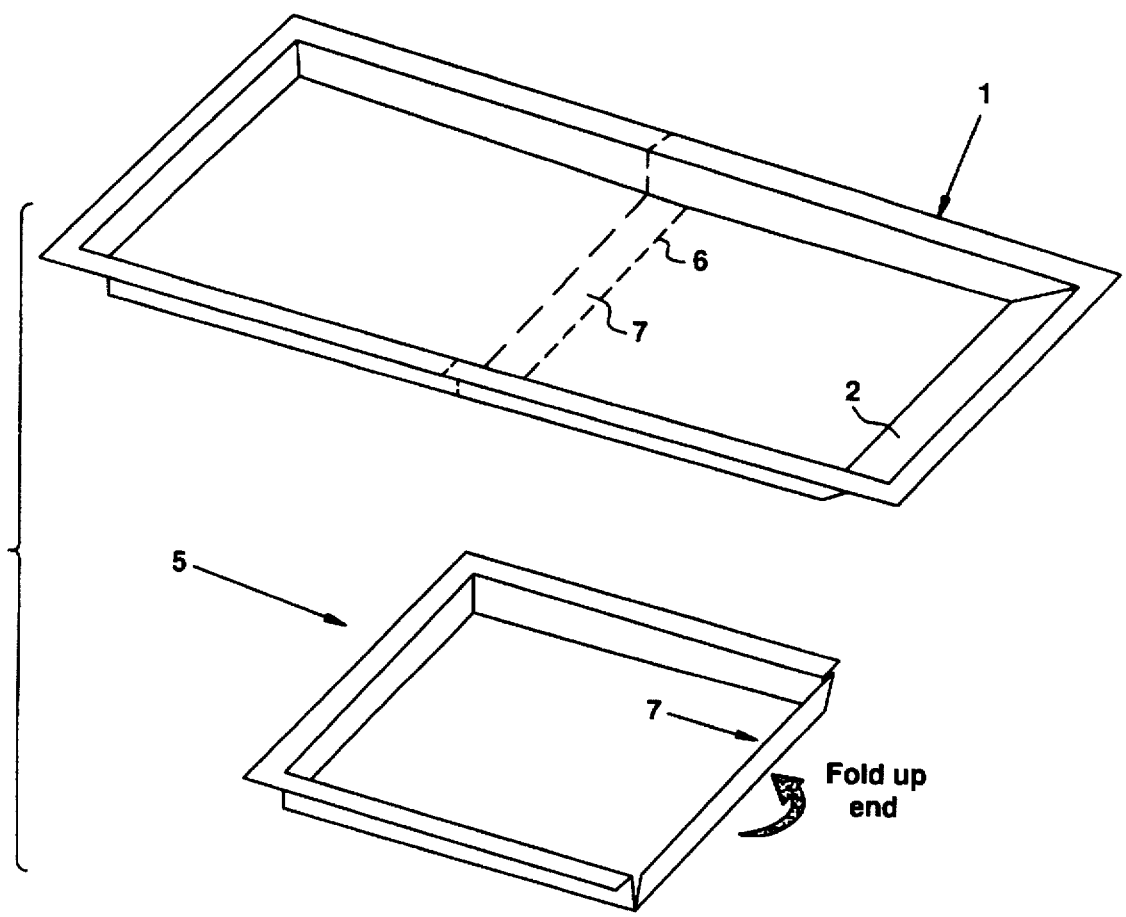
FIG. 3 shows a tray of FIG. 1 modified in order to fit into an electrophoresis tank.

The container in which lane by lane support medium is prepared is preferably a tray 1. FIG. 3. The tray is preferably made of ultra violet light transmissible material. For enhancing ultra violet transmission of the tray, windows or perforations may be provided in bottom of the tray. For facilitating transfer of gel lanes out of the tray 1, preferably, one side wall of the container tray has sloped wall 2 ( as shown in FIG. 1 & FIG. 3). The gel lanes can easily slide over the slope 2 and move out of the tray, FIG. 2. The container tray may also be provided with scoops or similar devices for assisting removal and transfer of gel lanes.

Figure 4:
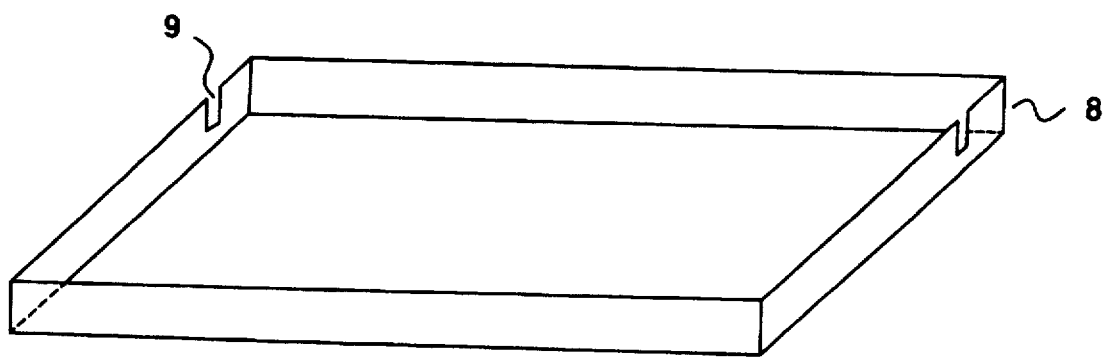
FIG. 4 shows a tray for holding gel support medium or another tray.
Figure 5:
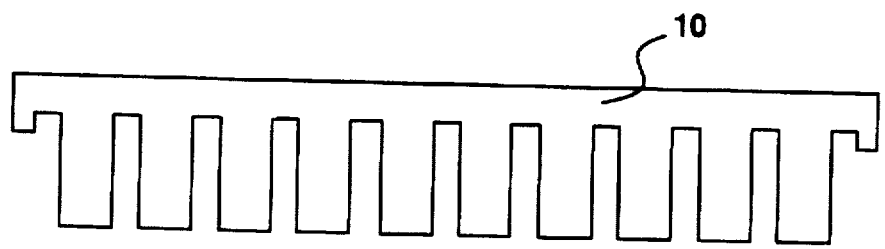
FIG. 5 shows a gel comb for formation of sample loading wells.

For making agarose electrophoresis support medium in lane by lane formation or into individual gel lanes, molten agarose is poured in a try. FIG. 4 shows an embodiment of a tray 8 having notches 9 for positioning gel combs 10. Other types of trays may also be used. FIG. 3 describes an alternative embodiment of the try 1 in which one of the side walls slopes outwardly 2. The tray 1 of FIG. 3 can be positioned into the tray 8 in which case the tray 8 of FIG. 4 acts as housing tray for the tray 1. Molten agarose is preferably poured into the tray 1, housed in the tray 8. A mold for creating sample loading wells 4, i.e. a gel comb as shown in FIG. 5, is positioned in the tray 8. When agarose solidifies into a slab gel support medium the gel comb 10 is removed. The slab gel support medium is cut into lane-by-lane formation or into individual lanes using gel slicing means shown in FIGS. 6 and 7.

Figure 6:
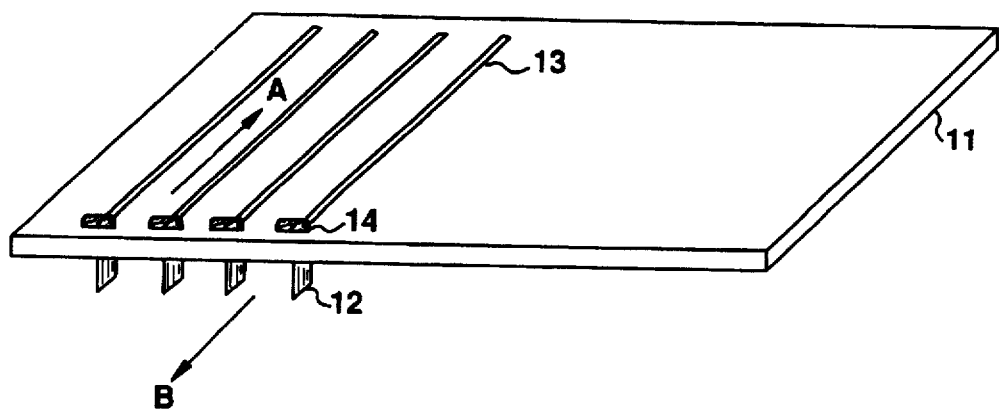
FIG. 6 shows a slicing means for cutting electrophoresis support medium into individual lanes.

FIG. 6 shows an embodiment of gel slicing means for cutting slab gel support medium into individual gel lanes. The gel slicing means of FIG. 6 consists of a plate 11 having plurality of short knife blades 12. The plate is large enough to cover the slab gel support medium formed in tray 1. The plate 11 may be provided with slits 13 for allowing the knife blades 12 to be traversed along the slits (in the direction of an arrow A) to cover the entire width or length of the slab gel support medium. The knife blades 12 are positioned into the slits 13 with a stud 14, and the studs can be used to drag the blades 12 along the slit 13. The plate may be provided with one or more blade 12. FIG. 6 shows only partial view of the device and shows only four blades, more blades may be added.

Figure 7:
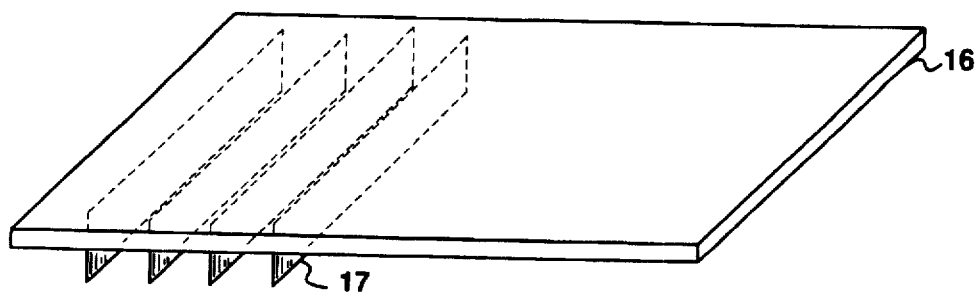
FIG. 7 shows an alternative embodiment of slicing means where by gel support medium is cut into individual gel lanes.
Figure 8:
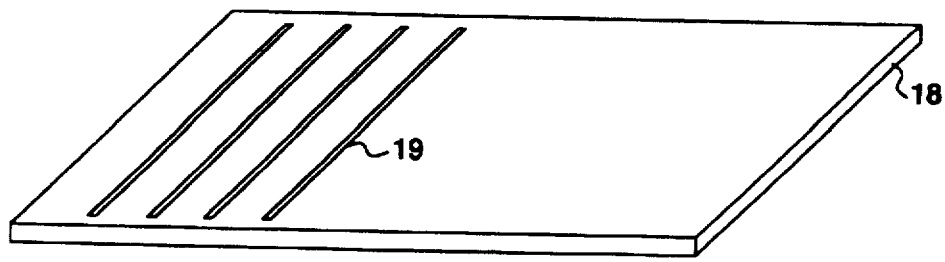
FIG. 8 shows gel lane ejection plate for the slicing means shown in FIG. 7.
Figure 9A:
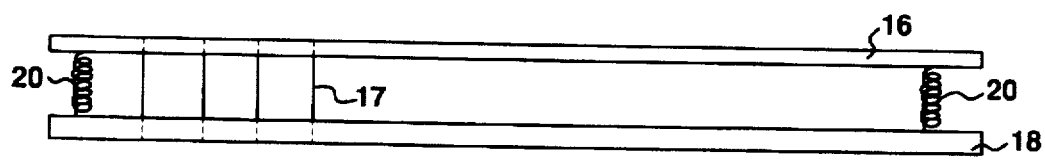
FIG. 9(A&B) shows a cross sectional views of the slicing means assembled with the ejection plate, as shows in FIGS. 7 and 8.
Figure 9B:
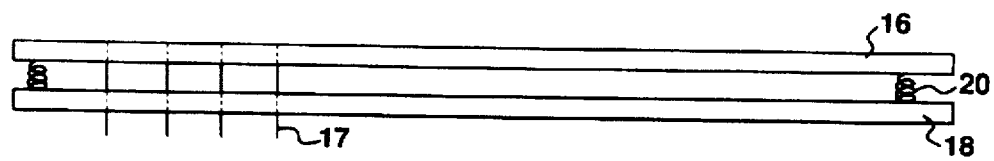

FIG. 7–9 show an alternative embodiment that can be used to cut slab gel support medium into individual lanes 3 as shown in FIGS. 1 and 2. The device is provided with a punching plate 16 wide enough to cover the slab gel support medium formed in the tray 1. The punching plate 16 has embedded into the plate a plurality of blades 17 arranged parallel to each other. FIGS. 7–9 show only partial view of the device with only four blades, more blades may be added. The device may be provided with ejection plate 18, as shown in FIG. 8. The ejection plate 18 have slits 19 that will allow the blades 17 to freely pass through the slits 19. The punching plate 16 and ejection plate 18 are assembled on spring loaded devices 20, as shown in the cross section view in FIG. 9A. When pressure is put on the punching plate 16, the blades passes through the slits 19 provided in the ejection plate 18 and emerge the other end of the ejection plate, as shown in FIG. 9B. When pressure is relieved, the spring 20 allows the blades to retract through the ejection plate 18.

The devices shown in FIG. 6 and FIG. 7 and can be positioned on the tray 8 either by hinging on the side of the tray or positioned over the tray using poles or other means such that the slicing devices can be lowered on the tray 8.

For cutting the slab gel support medium formed in the tray 1 (or tray 8), the tray 1 is returned into the housing tray 8 (gel comb 10 is removed). The gel can be cut into individual lanes using either the slicing device shown in FIG. 6 or the punching device shown in FIGS. 7–9.

In order to use the slicing device of FIG. 6, the plate 11 is lowered on the tray 8, allowing the blade knife 12 to pierce through the support medium formed in the tray 1. The position of the blades 12 are such that they locate between sample loading wells 4. The gel support medium is cut into individual lanes by pulling the housing tray 8 outwardly, (out of the plate 11) in the direction of arrow B, FIG. 6. Alternatively, the support medium may also be cut into individual lanes by dragging the studs 14 having knife 12 through the slit 13 in the direction of arrow A. The knife 12 slice through the slab gel support medium in the direction of an arrow A, FIG. 6.

For using the punching device of FIGS. 7–9, the punching plate 16, preferably assembled with the ejection plate 18 as shown in FIG. 9A is lowered on the housing tray 8. Jerking pressure (rapidly crushing) is applied on the punching plate 16. The blades 17, traverse through the slits 19 and strike the gel support medium in the tray 1, cutting slab gel into individual lanes. The spring 20 back pressure retracts the blades 17 through the ejection plate 18, ejecting gel lanes. Lane by lane format electrophoresis support medium may also be prepared by pouring gel as individual lanes (in trays or casts having individual lane format), as compared to pouring a slab gel and cutting it into individual lanes.

After cutting the slab gel into lane-by-lane formation or in individual lanes 3, each lane contains one sample loading well. However, the gel lane may be prepared to contain more than one sample loading wells side by side but it should be realized that as more sample loading wells are added to each lane it begins to reduce economic advantage of make gel in lane by lane formation. Up to two sample wells side by side in each lane is highly preferred or to a maximum of 3 sample wells side by side in each gel lane. More then three sample wells side by side in each lane will have very little flexibility of saving gel support medium.

Figure 10A:
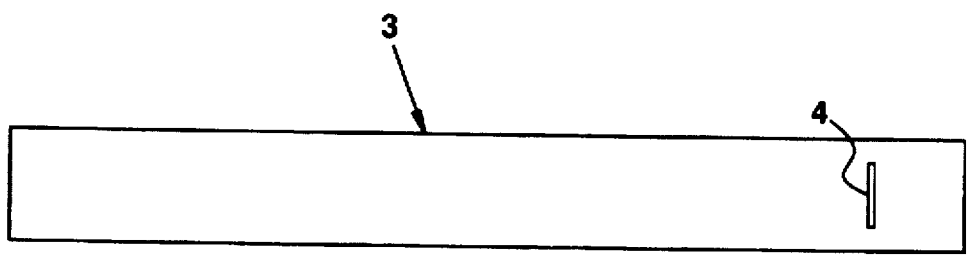
FIG. 10(A&B) shows individual gel lanes having one or two sample loading wells, facing each other.
Figure 10B:
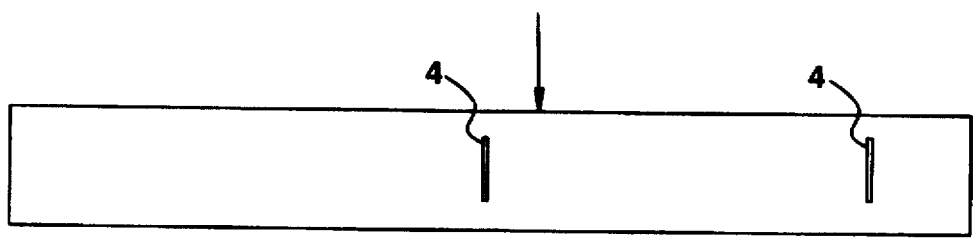

Sample loading wells may also be placed facing each other as in FIG. 10B. Slab gel support medium may be sliced twice, once across the width and a second time across the length, in the direction of arrow, as shown in FIG. 10B. FIG. 1 shows a container tray containing a formation of individual gel lanes 3 and each lane containing a sample well 4. After cutting agarose into lane-by-lane formation, the gel lane assembly may be stored for future use by placing the tray 1 in a liquid tight container or bag. Ethidium bromide or other antibacterial agents may be added to the agarose to prolong storage life of gel lanes.

For performing electrophoresis, one or more gel lanes are transferred from the container tray to an electrophoresis device, as shown in FIG. 2. The lanes are easily transferred by holding the tray at an angle (about 45° angle), or slopped over the device receiving the gel lanes and gently pushing the gel lanes to slide over the slopped side wall 2 of the tray 1 into the device receiving the gel lanes. The gel lanes are stacked together to one side of the electrophoresis platform, the gel lanes are positioned in the electrophoresis tank longitudinally between two electrodes, the sample loading wells facing toward the (-)terminal. After stacking a plurality of gel lanes the whole formation of gel lanes appears as a contiguous gel slab. Samples are loaded into the wells for electrophoresis.

In order to facilitate transfer and handling of gel lanes, an empty tray 1 (FIG. 3) may be adapted or modified to fit into an electrophoresis device and receive gel lanes for electrophoresis. FIG. 2 and FIG. 3 show the container tray of FIG. 1 modified into a smaller tray 5, by cutting away the tray from the end having slopped wall 2. FIG. 3 shows measuring the tray to fit into electrophoresis tank and cutting the tray 1 along the cut line 6 and folding up the end 7 into a tray 5.

Alternatively, a gel lane holding tray cassette or tray may be provided, comprising: a horizontal platform having barriers around all four sides; and an additional means to facilitate the stacking of a plurality of gel lanes to one side of the tray and firmly holding the gel lanes in stacking formation during electrophoresis.

Yet another objective of the present invention is to provide for recovery of gel bands after electrophoresis and extraction of molecules therein. After electrophoresis and localizing the gel bands of interest, the gel bands can be easily recovered by simply cutting out the band from the gel lane. Alternatively, the molecules in the gel bands can be electroeluted by cutting off the support medium in front of the band of interest and capping the gel lane including the gel band with a closure means described in the pending U.S. patent application Ser. No. 08/063,371, filed May 20, 1993 now U.S. Pat. No. 5,291,3 and 08/221,109, filed Mar. 31, 1994 now U.S. Pat. No. 5,635,049. (herein incorporated by reference). The closure means is sized to form liquid impervious relationship with the support medium of the gel lane i.e. gel lane plugs into the closure means. After electrophoresis the electroeluted molecules will be recovered from the closure means.

I claim:

1. A method of horizontal gel electrophoresis comprising the following steps:
   providing gel support medium as individual gel lanes;
   transferring one or more said gel lanes to an electrophoresis gel apparatus; and
   loading samples in said gel lanes and applying current for electrophoresis separation.

2. A method according to claim 1 wherein each gel lane contains at least one sample loading well.

3. A method according to claim 2 wherein each gel lane contains up to a maximum of three sample loading wells side by side.

4. A method according to claim 2 wherein each gel lane contains sample loading wells facing one another.

5. A method according to claim 1 wherein gel support medium is agarose.

6. A method according to claim 1 wherein gel lanes are provided in a tray like container, tray is provided with a sliding means in order to slide gel lanes out of the tray.

7. A method according to claim 6 wherein the container have at least one sloped wall for sliding gel lanes out of the tray.

8. A method according to claim 6 wherein the container is made of material that does not glow and transmit under ultra violet light.

9. A device for assisting horizontal gel electrophoresis, comprising:
   a container having gel support medium, said gel support medium is provided as a plurality of individual gel lanes, each gel lane having at least on sample loading well, said container is provided with a sliding means in order to slide gel lanes out of the container.

10. The device according to claim 9 wherein the container is made of material that does not glow and transmit under ultra violet light.

11. A device for cutting slab gel support medium in to individual lanes, comprising:
   a tray for receiving molten agarose having means for positioning a gel comb for forming sample loading wells;
   a gel slicing means for positioning over the tray to slice the support medium into individual lanes, the slicing means having plurality of knifes for cutting slab gel support medium into individual lanes.

12. A device according to claim 11 wherein, slicing means are capable of traversing across the slab gel support medium for cutting gel support medium into individual lanes.

13. A device according to claim 11 wherein, slicing means are punched over the slab gel support medium for cutting gel support medium into individual lanes.

* * * * *